(12) United States Patent
DiStefano et al.

(10) Patent No.: US 8,182,495 B2
(45) Date of Patent: May 22, 2012

(54) SUTURE TENSIONER WITH GAUGE

(76) Inventors: James G. DiStefano, San Francisco, CA (US); Andrew Park, San Francisco, CA (US)

( * ) Notice: Subject to any disclaimer, the term of this patent is extended or adjusted under 35 U.S.C. 154(b) by 374 days.

(21) Appl. No.: 12/506,295

(22) Filed: Jul. 21, 2009

(65) Prior Publication Data
US 2011/0022054 A1  Jan. 27, 2011

(51) Int. Cl.
*A61B 17/04* (2006.01)
(52) U.S. Cl. ............................ 606/144; 606/139
(58) Field of Classification Search .................. 606/139, 606/144, 147–150, 205–211
See application file for complete search history.

(56) References Cited

U.S. PATENT DOCUMENTS

| | | | |
|---|---|---|---|
| 3,980,086 A * | 9/1976 | Kletschka et al. | 604/35 |
| 4,961,741 A | 10/1990 | Hayhurst | |
| 5,035,701 A * | 7/1991 | Kabbara | 606/148 |
| 5,395,367 A * | 3/1995 | Wilk | 606/1 |
| 5,474,057 A * | 12/1995 | Makower et al. | 600/214 |
| 5,501,690 A | 3/1996 | Measamer et al. | |
| 5,741,281 A | 4/1998 | Martin | |
| 5,759,189 A | 6/1998 | Ferragamo et al. | |
| 6,010,515 A | 1/2000 | Swain et al. | |
| 6,086,601 A | 7/2000 | Yoon | |
| 6,358,259 B1 | 3/2002 | Swain et al. | |
| 6,557,426 B2 | 5/2003 | Reinemann, Jr. et al. | |
| 6,866,673 B2 | 3/2005 | Oren et al. | |
| 7,343,791 B2 | 3/2008 | Cuevas et al. | |
| 2007/0060931 A1 | 3/2007 | Hamilton et al. | |

\* cited by examiner

*Primary Examiner* — Corrine M McDermott
*Assistant Examiner* — Gregory Anderson
(74) *Attorney, Agent, or Firm* — Bernhard P. Molldrem, Jr.

(57) ABSTRACT

A tensioner for a tightening a surgical knot has a squeeze handle and a pair of jaw arms that pivot from a common point behind the handle. The jaw arms have a jaw clamp at the distal tip to clamp onto the suture material, and a release handle at the proximal or butt end. A spreader or distractor mechanism may be a pantographic arrangement of struts joined to anchor points on the jaw arms. This converts axial motion of an actuator rod into a lateral distractive force. A tension gauge in the handle indicates the amount of tension being applied to the suture material.

10 Claims, 2 Drawing Sheets

SUTURE TENSIONER WITH GAUGE

BACKGROUND OF THE INVENTION

This invention relates to suture-tying instruments for surgical use, and is more particularly concerned with a tensioning device to be employed in tightening a surgical knot formed in suture material.

The invention is more favorably embodied in a hand-held surgical device that permits the surgeon to apply a controlled, optimal amount of tension onto a surgical knot, appropriate to the patient's tissue that is being closed by a stitch, and to the type of suture material being used.

As a part of a surgical procedure, sutures are placed in the patient's tissue for holding cut tissue surfaces in apposition for a period of time appropriate for healing. Many types of suture material are employed, depending upon the type of tissue and on the type of surgery. A variety of absorbable and non-absorbable materials are available. Each type of material has its own strength and flexibility characteristics, and so the amount of tension needed to complete the suture knot can vary widely.

At present, the surgeon does not have any knot-making apparatus available to apply the optimal tension to the suture knot.

Once a non-locking suture knot has been placed, the surgeon needs to tension the knot, grasping the free ends of the suture material and pulling them, with sufficient force to complete the desired aim, but without over-tensioning the suture, which may damage the material or the patient's tissue.

OBJECTS AND SUMMARY OF THE INVENTION

Accordingly, it is an object of this invention to provide a surgical device that will facilitate surgical knot-tying with the tension that is appropriate for the suture material and for the patient's tissue.

It is another object to provide a surgical tool that converts the controlled force of hand pressure into the desired tension to complete the surgical knot.

A further object is to provide a surgical instrument with an included tension gauge or meter, so that the amount of tension being applied to the surgical knot can be measured and controlled.

In accordance with an aspect of this invention, a suture-tensioning clamping device applies a controlled tensile force onto the suture material on either side of the suture knot. A frame of the device has a grip handle and a squeeze lever that can be hand-squeezed to move towards the aid grip handle. A pivot pin or post is affixed at a proximal or butt end of the frame, and an actuator rod extends distally from the frame and moves in response to hand pressure on the squeeze lever. A pair of jaw arms extend forward from a pivot post or pin on the frame. Each of the jaw arms has a pivot passage at its proximal end adapted to fit pivotally onto the pivot pin. Each jaw arm also has a suture jaw clamp at its forward or distal end, and the jaw clamp is opened and closed to secure the suture material. An attachment member disposed between the proximal and distal ends of the jaw arm so that it can be pushed outward to pull the knot tight. A mechanical spreader mechanism is operatively coupled to the attachment members of said jaw arms and to said actuator rod. The spreader mechanism applies a sideward tensile force (i.e., a distractive force) to the pair of jaw arms in response to hand pressure on the squeeze lever, and with the corresponding movement of the rod. This causes the jaw arms to pivot and distract outwards, that is, to pivot on the pivot pin and move away from one another so as to place a tension to the suture knot.

Favorably, each of the jaw arms has a release handle at its proximal end which is actuated to open and close the associated suture jaw clamp. The jaw arms may both be removably fitted onto the same pivot pin, and a removable retaining cap on hold the jaw arms in place on the pivot pin. The jaw arms each include a pivot member, i.e., an ear or arm, extending a short distance laterally at the proximal end of the jaws arm, and the pivot passage is formed in this pivot member.

A tension gauge is positioned on handle or frame and is operatively coupled with the actuator rod. A digital or analog visible indicator displays the tensile force applied between the two jaw arms.

In a preferred arrangement, the mechanical spreader mechanism is in the form of a pantographic mechanism, i.e., a double-action hinged arrangement. That mechanism may be coupled to each of the jaw arms and to the actuator rod, for converting distal force of the rod into sidewards tensile force (outward motion of the two jaw arms), applying spreader force by scissors action. Favorably, the pantographic mechanism includes at least a pair of struts having first ends pivotally joined to a distal end of the actuator rod. The other ends of the struts are then pivotally joined to respective pivot members on left and right ones of the jaw arms.

In the suture tightening clamp of this invention, after a non-locking suture knot has been placed, the device will allow the surgeon to grasp and secure the free ends of various types of suture material in the clamping jaws. The clamp jaws can be individually controlled. The suture grasping jaws function on a hinge mechanism, each jaw arm having the clamp jaw attached on a sliding mechanism to control the opening and closing of the clamp jaw. The proximal ends of the jaw arms, i.e., the ends remote from the clamp jaws, share a common pivot axis, so that they move towards and away from each other about their common rotational axis. The opening and closing of the arms is effected by a central double-action hinge mechanism, i.e., the aforesaid pantograph mechanism.

The hand-squeeze mechanism in the frame or handle produces the distraction between the two jaw arms. This can have either of two types of action. In one design, compression of the dynamic squeeze handle towards the fixed handle involves a cranking mechanism for stepwise increase in the tension applied. Compression of the dynamic squeeze handle and then allowing it to return to its initial position constitutes one cycle, and several squeezes or cycles may be needed to apply sufficient tension to the suture knot. Squeezing the actuator handle a number of times will result in the maximum achievable distraction.

A second type of squeeze mechanism can rely on the manual force of squeezing directly to move the actuator rod into the double-action hinge or pantograph mechanism. Rather than a stepwise increase in tension, a continuous distraction will be produced along a single contraction cycle of the squeeze handle.

The included tension gauge or tensiometer provides a measure of the force applied onto the suture material. The tension gauge correlates with the distractive force felt between the two jaw arms. After a desired distraction and/or tension is achieved, and the knot is secured (with a separate clamp), a release button will relieve the tension across the arms. A separate release handle or button then relieves the jaw clamps to release the free ends of the suture material, and the device can be removed to tighten the next suture knot.

Surgical grade stainless steel is preferred, to allow for heat sterilization and operating room use. In some applications, a durable surgical grade plastic resin may be used, with the device being intended for use on a single patient and then discarded.

The above and many other objects, features, and advantages of this invention will become apparent to persons skilled in the art from the ensuing description of a preferred embodiment, which is to be read in conjunction with the accompanying Drawing.

DETAILED DESCRIPTION OF THE PREFERRED EMBODIMENT

Figure 1:
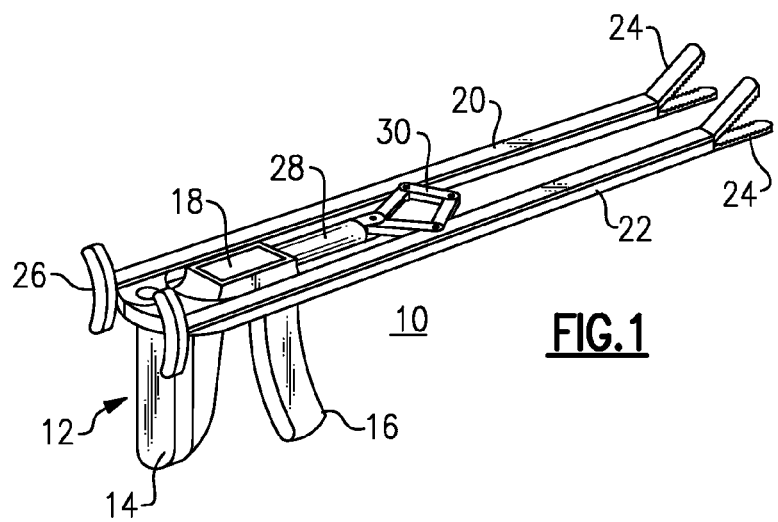
FIG. 1 is a perspective view of a suture tying tensioner, according to one possible embodiment of this invention.

With reference to the Drawing, and initially to FIG. 1, a surgical knot tightening apparatus or suture tensioner 10 that embodies this invention is a hand-held device that employs the controlled force of a hand squeeze to distract or pull apart the two free ends of suture material where a suture knot is to be tied. The tensioner 10, also shown in FIG. 2, has a frame 12 in the form of a handle, with a fixed handle grip 14 and a squeeze lever 16, which are at the under side of the frame. A tension gauge 18 is incorporated into the top part of the frame, and may have a digital display that indicates quantitatively the amount of tensile force that is being applied to the suture material.

There is a left jaw arm 20 and a right jaw arm 22, which are pivotally supported from the proximal or butt end of the tensioner frame 12. In this embodiment, these jaw arms are straight, thin members, and each of them has a suture clamp jaw 24 at its forward or distal end. In other embodiments, the two jaw arms may be other shapes or configurations, with curvatures and sizes to allow the device to function in various spaces within the body. An actuator handle 26 at the proximal end of each of the jaw arms 20 and 22 is pulled or twisted to close or release the respective clamp jaw 24. An actuator rod or push rod 28 extends distally, i.e., forward, from the frame 12, and moves in response to hand pressure on the squeeze lever 16. The rod 28 is connected with a lateral spreading mechanism 30, here in the form of a quadrilateral hinged design, i.e., a pantograph mechanism, that is also attached to anchor points on the two jaw arms 20 and 22. The spreading mechanism will be discussed in more detail below.

Figure 2:
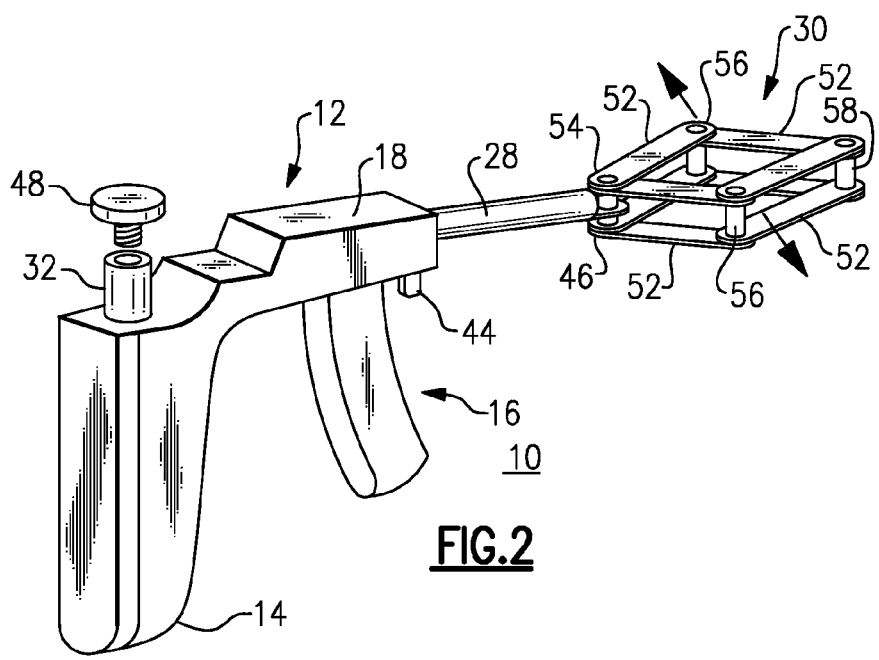
FIG. 2 is partial perspective of the tensioner of this embodiment.

A pivot post 32 or pivot pin, shown in FIG. 2, is formed or installed at the butt or proximal end of the frame 12, and serves as a mount and a pivot for the jaw arms 20 and 24.

Figure 3:
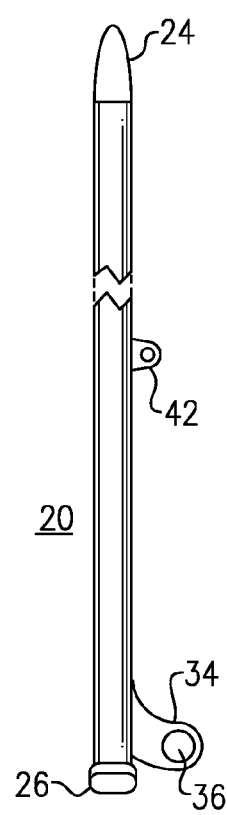
FIG. 3 is a plan view of the left-side jaw arm of this embodiment.
Figure 5:
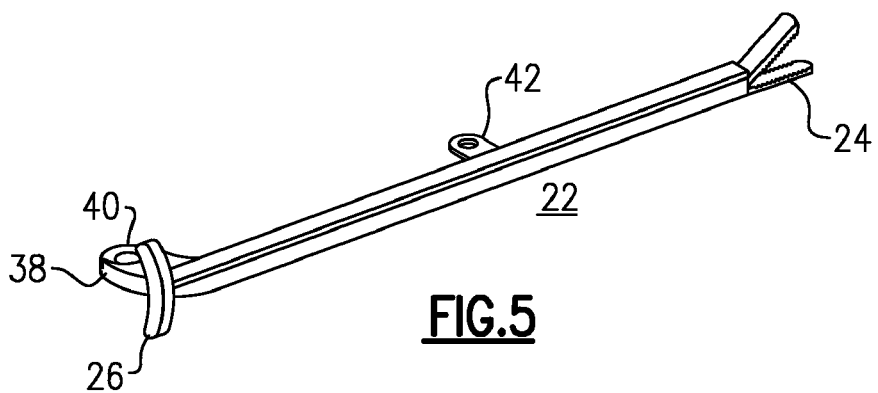
FIG. 5 is a perspective view of the right-side jaw arm of this embodiment.

The jaw arms 20 and 22 are shown in more detail in FIGS. 3 and 5, respectively. The left jaw arm 20 has a pivot ear or flange 34 extending to the side from its proximal end, and the pivot ear 34 has a pivot passage 36 or round bore that fits over the post 32. Likewise, the right jaw arm 22 has a pivot ear 38 with round pivot passage 40 that also fits over the post 32. In each case, there is a pivot anchor 42 extending the side of the jaw arm about midway between its proximal and distal ends. The spreading mechanism 30 attaches to each of these pivot anchors 42.

Returning to FIG. 2, on the frame near the squeeze lever 16 is a release lever or release handle 44 which can be pushed to release the force on the rod 28 and to relieve the distraction force between the two clamp jaws 24. At the distal end of the rod 28 is a nose plate 46, which has an aperture through it to receive an attachment pin of the spreading mechanism 30. A screw-on retaining cap or retaining nut 48 attaches onto the end of the pivot post 32 atop the two pivot ears 34, 38, which are positioned one atop the other on the post 32. In other embodiments, the two jaw arms 20 and 24 could be pivotally supported on two separate pivot posts.

Figure 4A:
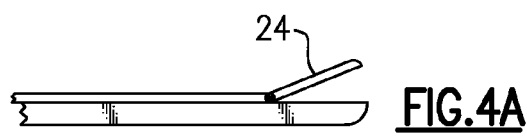
FIGS. 4A and 4B are illustrations of the distal end of the jaw arm with the jaw clamp in the open and closed position, respectively.
Figure 4B:
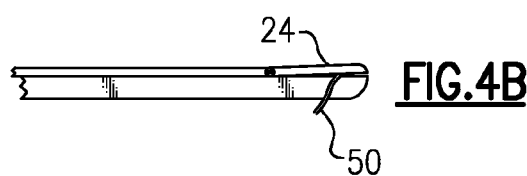

FIGS. 4A and 4B respectively illustrate the distal tip of one of the jaw arms with the associated clamp jaw 24 in its open position and in its closed position, clamping on a length of suture wire 50. A twist or pull on the associated actuator handle 26 moves the clamp jaw 24 between its closed and released positions.

The spreader mechanism 30 in this embodiment is a quadrilateral hinged device, sometimes referred to as a pantograph device. The device is formed of four pairs of struts 52 arranged the struts of each pair are positioned one above another and the four pairs form a diamond shape, the struts 52 being connected with pivot pins. A center pivot pin 54 joins the two proximal pairs of struts 52 to the nose plate 46 of the actuator rod 28, and two side pivot pins 56 connect the side corners of the device to the anchors or pivot members 42 of the two jaw arms 20 and 22. At the center distal corner, a fourth pivot pin 58 is a free pin, and serves to stabilize the action.

Figure 6A:
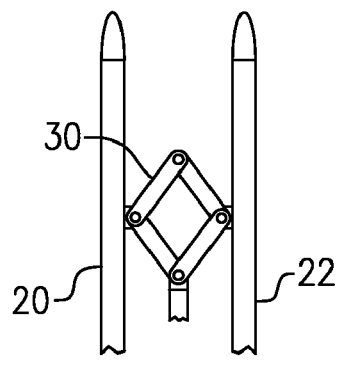
FIGS. 6A and 6B are partial top views of the tensioner of this embodiment, showing the jaw arms in an undistracted position and in a distracted position, respectively.
Figure 6B:
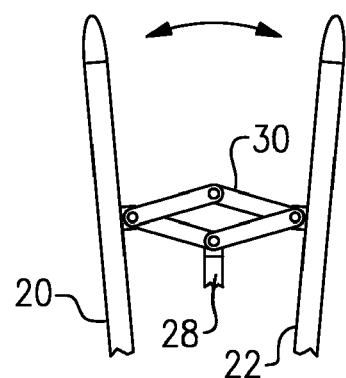

As explained with reference to FIGS. 6A and 6B, distal or forward movement of the actuator rod 28 pushes the diamond shape of the device 30 so that the two pins 56 spread apart and push the two jaw arms 20 and 22 away from one another. Pushing on the release lever 44 relieves the force on the actuator rod, and it can then return to the proximal, so that the spreader mechanism 30 resumes the shape of FIG. 6A, allowing the distal tips of the arms to move back and relieve tension on the suture material.

Figure 7:
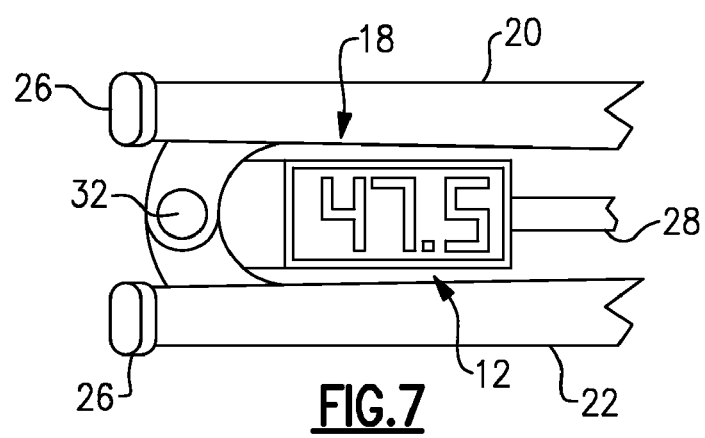
FIG. 7 is a partial top view of the proximal end of the tensioner, showing the tension display.

FIG. 7 shows the top of the frame 12 at the handle or proximal end of the instrument 10, and here shows the tension gauge 18 to have a digital display. The gauge is calibrated to provide a measure of the suture tension based on the force on the actuator rod 28 and the position of the rod. This provides useful information to the surgeon so that the sutures will have the proper tension applied in respect to the suture material and operative use. Rather than the digital tension gauge, a linear analog indicator device an be used to measure and display suture tension. This can e.g. be in the form of a needle moving in a linear fashion, with a tension-marked scale on one side of the device. The indication can also be remoted to a computer, by cable or wirelessly.

The suture tensioner 10 of this invention is applied after the surgeon has placed a non-locking suture knot through the apposed sides of the cut in the patient's tissue. The device is placed on the free ends of the suture material on either side of the knot. The jaw clamps 24 are closed over the suture material 50. Each jaw can be manipulated individually, using the actuator handles 26. Then, the surgeon can gently apply hand pressure onto the squeeze lever 16, to produce tension, via the pantograph device 30 and the two jaw arms 20 and 22, on the suture material 50 to pull the knot tight. In one preferred design, the tensioner 10 has an internal stepwise cranking mechanism within the frame 12. Compression of the dynamic squeeze lever 16 applies a unit of motion to the rod 28, and then the lever 16 is released to return to its original position. This constitutes one cycle, and the surgeon applies a sufficient number of cycles to achieve the proper tension on the suture. With each cycle of compression of the cranking mechanism, the tips of the jaw arms will distract a given amount, causing the distance between the jaw clamps 24 at the tips of the arms to increase, until a maximum excursion distance is achieved, governed by the geometry of the pantograph device 30. The device can be constructed such that there is a predetermined increment of tension added for each cycle of the stepwise cranking mechanism.

In a second, alternative embodiment, the manual force of squeezing the lever 16 directly moves the actuator rod 28 distally, and distracts the jaw arms 20 and 22. That is, rather than a stepwise increase in tension, a continuous distraction is produced along a single contraction cycle of the lever 16.

The tension gauge 18 indicates the force generated, i.e., the amount of tension being applied to the suture. The tension gauge 18 correlates with the distractive force being felt between the two jaw arms 20 and 22. After the desired distraction, i.e., tension, is achieved, the knot is secured with a separate clamp (not shown). The release lever 44 is pushed to relieve the tension between the two jaw arms, and the actuator handles 26 are turned for the jaw arms to open the associated jaw clamps 24. This releases the suture so the device can be removed, and the surgeon can complete the knot.

Preferably, the device is made of a surgical stainless steel, to allow sterilization for operating room use. However, where one-time use is appropriate, the device may be formed, completely or partly, of a disposable medical grade plastic.

Many other modifications and variations are possible which would not depart from the scope and spirit of this invention, as defined in the appended claims.

We claim:

1. A suture tensioning device for applying a controlled tensile force onto suture material on either side of a suture knot, comprising:
   a frame which includes a grip handle and a squeeze lever movable towards said grip handle, a pivot pin situated proximal of said squeeze lever, and an actuator member which extends distally from said frame and which moves in response to squeezing of said squeeze lever;
   a pair of jaw arms each having a pivot passage at a proximal end of the jaw arm adapted to fit pivotally onto the pivot pin on said frame; a suture jaw clamp at a distal end thereof and which is openable and closeable for securing to respective ends of said suture material; and an attachment member disposed between the proximal and distal ends thereof;
   a mechanical spreader mechanism coupled to the attachment members of said jaw arms; and to said actuator member; and adapted to apply a controlled sideward distractive force between said jaw arms in response to squeezing of said squeeze lever and corresponding movement of said actuator member, to cause the pair of jaw arms to pivot, on said pivot pin, away from one another and apply a distractive tension to said suture knot; and
   a tension gauge positioned on said frame and operatively coupled to said actuator member, to provide a measure of suture tension existing between said ends of the suture material, and including a visible indicator displaying the force of said suture tension as applied between said pair of arms.

2. The suture tensioning device of claim 1 comprising a release handle which is actuated to relieve said distractive force between said jaw arms.

3. The suture tensioning device of claim 1 wherein said jaw arms are removably fitted onto said pivot pin, and further comprising a removable retaining cap on said pivot pin.

4. The suture tensioning device of claim 3 wherein said pivot pin is a single pin positioned at a proximal end of said frame, and said jaw arms each include a pivot arm at a proximal end thereof in which the associated pivot passage is formed; and the pivot arms of both said jaw arms are positioned on said single pivot pin and retained by said retaining cap.

5. The suture tensioning device of claim 1 wherein said mechanical spreader mechanism includes a pantographic mechanism coupled to each of said jaw arms and to said actuator rod, for converting distal force of said rod into said sidewards tensile force of said jaw arms.

6. The suture tensioning device of claim 5 wherein said pantographic mechanism includes at least a pair of struts having first ends pivotally joined to a distal end of said actuator member, and having second ends pivotally joined to respective pivot members on left and right ones of said jaw arms.

7. The suture tensioning device of claim 6 wherein said pantographic mechanism includes third and fourth struts having first ends joined to the respective pivot members of said jaw arms, and second ends pivotally joined to one another by means of free pin to form a center distal corner of the pantographic mechanism.

8. The suture tensioning device of claim 1 wherein said frame includes a stepwise cranking mechanism responsive to compressions of said squeeze handle for advancing said actuator member in steps for respective compressions of said squeeze handle.

9. The suture tensioning device of claim 1 wherein said squeeze handle is coupled to said actuator member to create a continuous distractive force between said pair of arms along a single compression of said squeeze handle.

10. The suture tensioning device of claim 1 wherein at least the jaw arms thereof are formed of a durable surgical grade plastic resin, permitting the same to be used for a single patient and then discarded.

* * * * *